United States Patent [19]

Cawthorne

[11] Patent Number: 4,988,720
[45] Date of Patent: Jan. 29, 1991

[54] NOVEL TREATMENT OF HYPERGLYCAEMIA

[75] Inventor: Michael A. Cawthorne, Horsham, England

[73] Assignee: Beecham Group P.L.C., Middlesex, England

[21] Appl. No.: 336,241

[22] Filed: Apr. 11, 1989

Related U.S. Application Data

[62] Division of Ser. No. 866,307, May 23, 1986, Pat. No. 4,847,280.

[30] Foreign Application Priority Data

May 28, 1985 [GB] United Kingdom ............... 8513367
Aug. 17, 1985 [GB] United Kingdom ............... 8520651

[51] Int. Cl.$^5$ .................. A61K 31/42; A61K 31/47; A61K 31/55; A61K 31/425
[52] U.S. Cl. .................................. 514/377; 514/213; 514/309; 514/310; 514/370; 514/414; 514/422
[58] Field of Search ............... 514/377, 213, 310, 309, 514/370, 414, 422

[56] References Cited

U.S. PATENT DOCUMENTS

4,526,897  7/1985  Cohnen et al. ...................... 514/392

FOREIGN PATENT DOCUMENTS

0072954  3/1983  European Pat. Off. .
2021100  11/1979  United Kingdom .

Primary Examiner—Allen J. Robinson
Attorney, Agent, or Firm—Hopgood, Calimafde, Kalil, Blaustein & Judlowe

[57] ABSTRACT

A method for the treatment and/or prophylaxis of hyperglycemia in mammals including administration to the mammal of an effective, nontoxic amount of either a compound of formula (I),

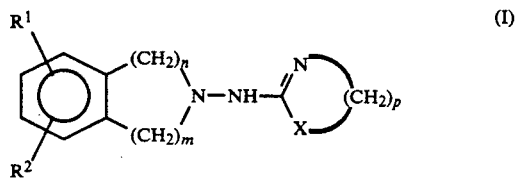

or a pharmaceutically acceptable acid addition salt thereof; or of a compound of formula (II),

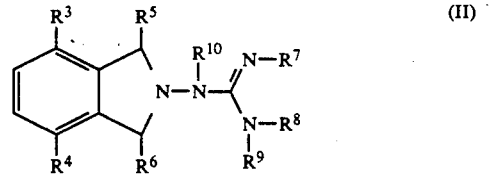

or a pharmaceutically acceptable acid addition salt thereof.

3 Claims, No Drawings

NOVEL TREATMENT OF HYPERGLYCAEMIA

This application is a divisional of Ser.No. 866,307 filed May 23, 1986 which has issued as U.S. Pat. No. 4,847,280.

The present invention relates to a method for the treatment and/or prophylaxis of hyperglycaemia and a composition for use in such method.

British patent application No. 2021100A discloses compounds of formula (A):

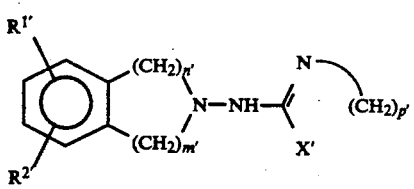

in which each of $R^{1'}$ and $R^{2'}$, which may be the same or different, represents a hydrogen or halogen atom, or an alkyl or alkoxy group containing 1 to 4 carbon atoms, $X'$ represents an oxygen or sulphur atom, an imino group, an acylimino group containing 2 to 4 carbon atoms in the acyl group, or a methylene group, each of n' and m', which may be the same or different, represents the number 1,2 or 3, and p' represents the number 2 or 3, as well as their physiologically acceptable acid addition salts. The compounds of formula (A) are described therein as having long lasting anti-hypertensive activity.

European Patent Number 0 072 954 discloses compounds of the general formula (B):

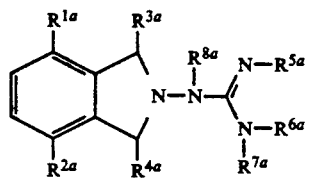

in which $R^{1a}$ and $R^{2a}$ can be identical or different and either hydrogen or a halogen, alkyl, or alkoxy, each with 1 to 4 carbon atoms, $R^{3a}$ and $R^{4a}$ can be identical or different and either a hydrogen or an alkyl with 1 to 4 carbon atoms, and $R^{5a}$, $R^{6a}$, $R^{7a}$, and $R^{8a}$ can be identical or different and either hydrogen or an alkyl with 1 to 4 carbon atoms, or in which $R^{5a}$ and $R^{6a}$ together represent the ethylene group, or their salts, except for 2-(N-aminoisoindolinyl)-imidazoline and 4-chloro-2-(2-imidazolin-2-ylamino)-isoindoline.

The compounds of formula (B) are disclosed therein as having long lasting hypertensive activity.

It has now been discovered that certain compounds of formula (A), including compounds which have been specifically disclosed in GB2021100A also have anti-hyperglycaemic activity, and are therefore of potential use in the treatment and/or prophylaxis of hyperglycaemia in mammals, including humans.

It has also been discovered that certain compounds of formula (B) have anti-hyperglycaemic activity and are of potential use in the treatment and/or prophylaxis of hyperglycaemia in mammals, including humans.

Accordingly, the present invention provides a method for the treatment and/or prophylaxis of hyperglycaemia in human or non-human mammals which comprises administering to the mammal in need of such treatment and/or prophylaxis an effective, non-toxic amount of: a compound of formula (I):

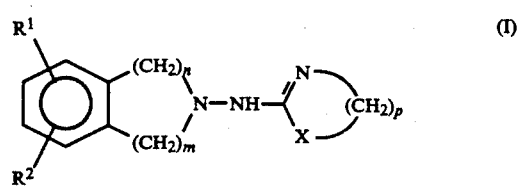

or a pharmaceutically acceptable acid addition salt thereof, wherein each of $R^1$ and $R^2$, which may be the same or different, represents a hydrogen or halogen atom, or an alkyl or alkoxy group containing 1 to 4 carbon atoms, X represents an oxygen or sulphur atom, an imino group, an acylimino group containing 2 to 4 carbon atoms in the acyl group, or a methylene group, each of n and m, which may be the same or different, represents the number 1, 2 or 3, and p represents the number 2 or 3; with the proviso that when the moiety

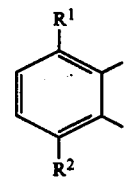

is present in formula (I), then either $R^1$ or $R^2$ must represent hydrogen; or a compound of formula (II):

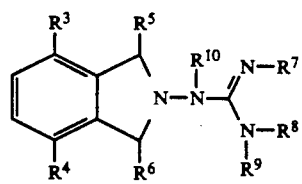

or a pharmaceutically acceptable acid addition salt thereof, wherein each of $R^3$ and $R^4$ may be either a hydrogen or halogen atom; or an alkyl or alkoxy group either of which groups may have from 1 to 4 carbon atoms; providing that either $R^3$ or $R^4$ must be hydrogen; $R^5$ and $R^6$ can be identical or different and either a hydrogen or an alkyl with 1 to 4 carbon atoms, and $R^7$, $R^8$, $R^9$, and $R^{10}$ can be identical or different and either hydrogen or an alkyl with 1 to 4 carbon atoms, or in which $R^7$ and $R^8$ together represent an ethylene group with the further proviso that when $R^7$ and $R^8$ represent an ethylene group then at least one of $R^5$, $R^6$, $R^9$ and $R^{10}$ represents an alkyl group with 1 to 4 carbon atoms.

One favoured sub-group of the compounds of formula (I) is that represented by the general formula (III)

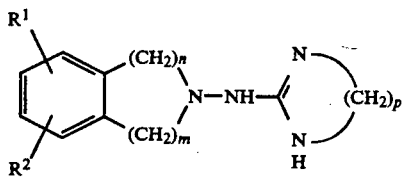

or a pharmaceutically acceptable acid addition salt thereof, wherein $R^1$, $R^2$, n, m and p are as defined in relation to formula (I).

A further preferred sub-group of the compounds of formula (I) is that represented by the general formula (IV):

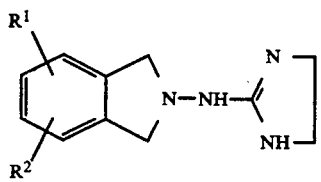

wherein $R^1$ and $R^2$ are as defined in relation to formula (I).

One particularly favoured sub-group of the compounds of formula (I) is that represented by the general formula (V):

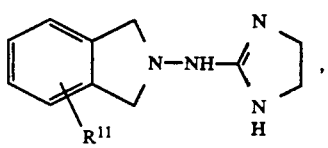

or a pharmaceutically acceptable acid addition salt thereof, wherein $R^{11}$ is hydrogen or chlorine.

Preferably, $R^{11}$ is substituted in the ortho position on the phenyl ring, relative to one of the —CH$_2$— moieties.

In a preferred aspect the compound of formula (I) is 4-chloro-2-(2-imidazolin-2-ylamino)isoindoline, or a pharmaceutically acceptable acid addition salt thereof.

In another preferred aspect the compound of formula (I) is 2-(2-imidazolin-2-ylamino)isoindoline, or a pharmaceutically acceptable acid addition salt thereof.

The present invention also provides a compound of formula (I) or formula (II), or a pharmaceutically acceptable acid addition salt thereof, for use in the treatment and/or prophylaxis of hyperglycaemia.

In a further aspect the invention also provides the use of a compound of formula (I) or formula (II), or a pharmaceutically acceptable acid addition salt thereof, for the manufacture of a medicament for the treatment and/or prophylaxis of hyperglycaemia.

In a further aspect of the invention there is also provided a pharmaceutical composition for use in the treatment and/or prophylaxis of hyperglycaemia which comprises a compound of formula (I) or formula (II), or a pharmaceutically acceptable acid addition salt thereof, and a pharmaceutically acceptable carrier therefor.

The compounds of formula (I) may be prepared using methods conventional in the art, for example those disclosed in GB2021100A.

The compounds of formula (II) may be prepared using methods conventional in the art, for example those disclosed in EP0,072,954.

Suitable pharmaceutically acceptable acid addition salts of the compounds of formulae (I) and (II), and the methods for preparing such salts, are disclosed in GB2021100A and EP0072954 respectively.

The administration to the mammal may be by way of oral administration or parenteral administration.

Preferably, the compound of formula (I) or formula (II), or a pharmaceutically acceptable acid addition salt thereof, (hereinafter called "the drug") is administered in the form of a unit-dose composition, such as a unit dose oral or parenteral composition. Such unit doses will normally comprise 0.1 to 1000 mg of the drug, more usually 0.1 to 550 mg.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the drug and a sterile vehicle. The drug, depending on the vehicle and the concentration, can be either suspended or dissolved. Parenteral solutions are normally prepared by dissolving the drug in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the drug is suspended in the vehicle instead of being dissolved and sterilised by exposure to ethylene oxide before suspending in the sterile vehicle. Advantageously, a surfactant or wetting agent is included in the composition to facilitate uniform distribution of the drug.

In treating hyperglycaemic humans the drug may be taken in doses, such as those described above, one to six, preferably one to 4, times a day in a manner such that the total daily dose for a 70 kg adult will generally be about 0.1 to 6000 mg, and more usually about 1 to 1500 mg and preferably 100 to 500 mg. In general a total daily dose of from about $1.0 \times 10^{-3}$ mg/kg to 100 mg/kg, more usually from about 0.1 mg/kg to 25 mg/kg and preferably from about 1 to 10 mg/kg may be used.

In treating hyperglycaemic animals, especially dogs, the drug may be administered by mouth, usually once or twice a day and at about 0.025 mg/kg to 25 mg/kg, for example 0.1 mg/kg to 20 mg/kg.

The following pharmacological data illustrate the activity of the drug in tests which are indicative of its potential use in the treatment of hyperglycaemia.

PHARMACOLOGICAL DATA

A. Diabetic Mice, Mid-day Blood Glucose Concentrations

C57B1/KsJ diabetic (db/db) female mice, 5–6 weeks old, were housed 5 per cage and fed on Oxoid rat and mouse breeders diet in powdered form for one week. At the end of this period, the blood glucose concentration at mid-day was determined for all mice. The animals continued to be fed on the powdered diet or were given the same diet supplemented with the test compound. After 7 days, the mid-day blood glucose of all mice was again determined.

The concentration of glucose in mid-day blood samples taken at the end of each treatment period are shown below as the mean (mM)±S.D. The comparable values for animals fed on the powdered Oxoid diet alone are also shown. Five mice were used for each treatment.

| TEST COMPOUND | CONTROL | TREATED | DOSE (mmol kg$^{-1}$ of diet) |
| --- | --- | --- | --- |
| 4-chloro-2-(2-imidazolin-2-ylamino)isoindoline | 24.9 ± 1.3 | 8.5 ± 3.5 | 3 |
| | 11.1 ± 5.7 | 4.4 ± 0.4 | 1 |
| 2-(2-imidazolin-2-ylamino)-isoindoline | 22.5 ± 3.4 | 13.0 ± 5.7 | 3 |
| | 22.5 ± 3.4 | 18.0 ± 3.0 | 1 |

B. Obese Mice, Oral Glucose Tolerance Test

C57B1/6 obese (ob/ob) male mice were housed 6 per cage and fed on powdered Oxoid rat and mouse breeders diet for at least one week. The mice then continued to receive the powdered diet alone, or that diet supplemented with test compound, for 8 days. After 8 days, all the mice were fasted for 5 hours prior to receiving an oral load of glucose (3 g/kg). Blood samples for glucose analysis were taken 0, 45, 90 and 135 minutes after glucose administration and the results are given below as the percentage reduction in area under the blood glucose curve as compared with the control group. Six mice were used for each treatment.

| TEST COMPOUND | % REDUCTION | DOSE (mmol kg$^{-1}$ of diet) |
| --- | --- | --- |
| 4-chloro-2-(2-imidazolin-2-ylamino)isoindoline | 52 | 3 |
| | 40 | 1 |
| 2-(2-imidazolin-2-ylamino)isoindoline | 38 | 1 |

C. Reversal of Adrenaline-Exacerbated Glucose Intolerance in Mice

CFLP female mice of about 25 g were fasted for 24 hours prior to receiving water (10 ml/kg) or the test compound by the oral route. Thirty minutes later, glucose (1 g/kg) and adrenaline (300 μg/kg) were injected subcutaneously. Blood samples for glucose analysis were taken serially from the tail of each mouse at 0, 30, 60, 90 and 120 minutes after dosing glucose and the results obtained are expressed below as the percentage reduction in the area under the blood glucose curve. The test compound treated groups were compared to the water dosed control group in each experiment. Six mice were used in each treatment group.

| TEST COMPOUND | % REDUCTION | DOSE (mmol kg$^{-1}$ of diet) |
| --- | --- | --- |
| 2-(2-oxazolin-2-ylamino)isoindoline | 37 | 20 |
| 2-(2-imidazolin-2-ylamino)-1,2,3,4-tetrahydroisoquinoline | 23 | 20 |
| 4-chloro-2-(2-imidazolin-2-ylamino)isodoline | 28 | 5 |
| 2-(2-imidazolin-2-ylamino)isoindoline | 29 | 5 |

Toxicology Data

No adverse toxicological effects were indicated in any of the above mentioned experiments.

I claim:

1. A method for the treatment of hyperglycaemia in human or non-human mammals which comprises administering to the mammal in need of such treatment an effective non-toxic amount of:

compound of formula (I):

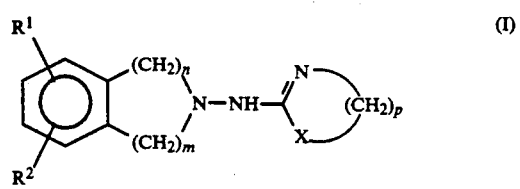

or a pharmaceutically acceptable acid addition salt thereof, wherein each of $R^1$ and $R^2$, which may be the same or different, represents a hydrogen, halogen atom, or an alkyl or alkoxy group containing 1 to 4 carbon atoms, X represents an oxygen, sulphur atom or a methylene group, each of n and m, which may be the same or different, represents the number 1, 2 or 3, and p represents the number 2; with the proviso that when the moiety

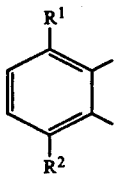

is present in formula (I), when either R¹ or R² must represent hydrogen.

2. A method according to claim 1, comprising the administration of a compound of the formulas (VI):

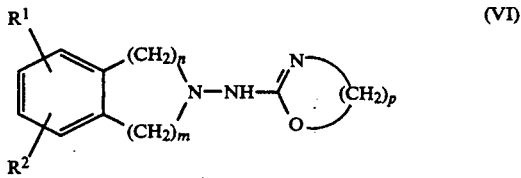

or a pharmaceutically acceptable acid addition salt thereof, wherein R¹, R², n, m and p are as defined in relation to formula (I).

3. A method according to claim 1, comprising the administration of 2-(2-oxazolin-2-ylamino) isoindoline, or a pharmaceutically acceptable acid addition salt thereof.

* * * * *